US00PP12401P2

(12) United States Plant Patent
Zimmermann

(10) Patent No.: US PP12,401 P2
(45) Date of Patent: Feb. 12, 2002

(54) HOP PLANT NAMED "YCR ACCESSION NO. 7"

(75) Inventor: Charles E. Zimmermann, Prosser, WA (US)

(73) Assignee: Yakima Chief Ranches, Inc., Sunnyvale, CA (US)

( * ) Notice: Subject to any disclaimer, the term of this patent is extended or adjusted under 35 U.S.C. 154(b) by 0 days.

(21) Appl. No.: 09/287,404

(22) Filed: Apr. 6, 1999

(51) Int. Cl.[7] ..... A01H 5/00
(52) U.S. Cl. ..... Plt./236

(58) Field of Search ..... Plt./236

*Primary Examiner*—Bruce R. Campell
*Assistant Examiner*—Anne Marie Grünberg
(74) *Attorney, Agent, or Firm*—Stratton Ballew PLLC

(57) ABSTRACT

The new hop plant variety is a bittering-type cultivar of recent origin. Its bittering and aromatic properties are similar to the Galena hop variety. However, unlike Galena which is susceptible to powdery mildew, the new variety is moderately tolerant to powdery mildew. It is also tolerant to Sphaerotheca. The new variety produces a medium size cone with fair to good pickability, and fair to good storageability. Harvest is medium-late, with a crop yield of 2450 to 2550 pounds per acre (2750 to 2860 kg/ha).

6 Drawing Sheets

BACKGROUND AND SUMMARY OF INVENTION

This invention relates to a new and distinct variety of hop plant, and more particularly to a new hop plant variety of unknown parentage which was discovered among plants created as part of a controlled breeding program. The new variety has been stably reproduced over successive generations. Discovery of the new variety and initial reproduction by root cuttings was carried out in a research nursery in Prosser, Wash., U.S.A. Subsequent asexual reproduction took place in Granger, Wash., U.S.A.

THE DRAWINGS

DESCRIPTION OF THE VARIETY

Figure 1:
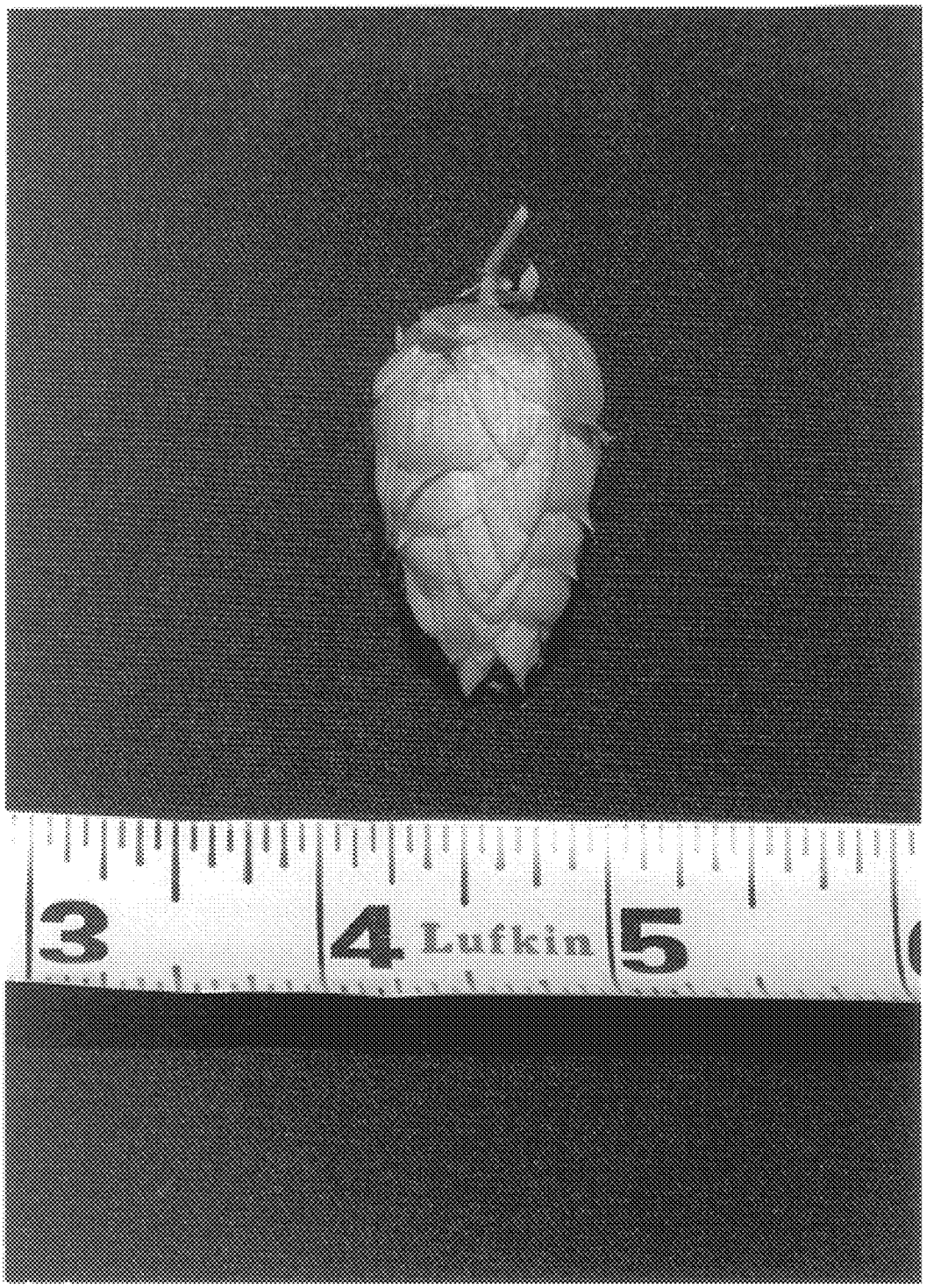
FIG. 1 shows a hop cone of the new hop plant variety.
Figure 2:
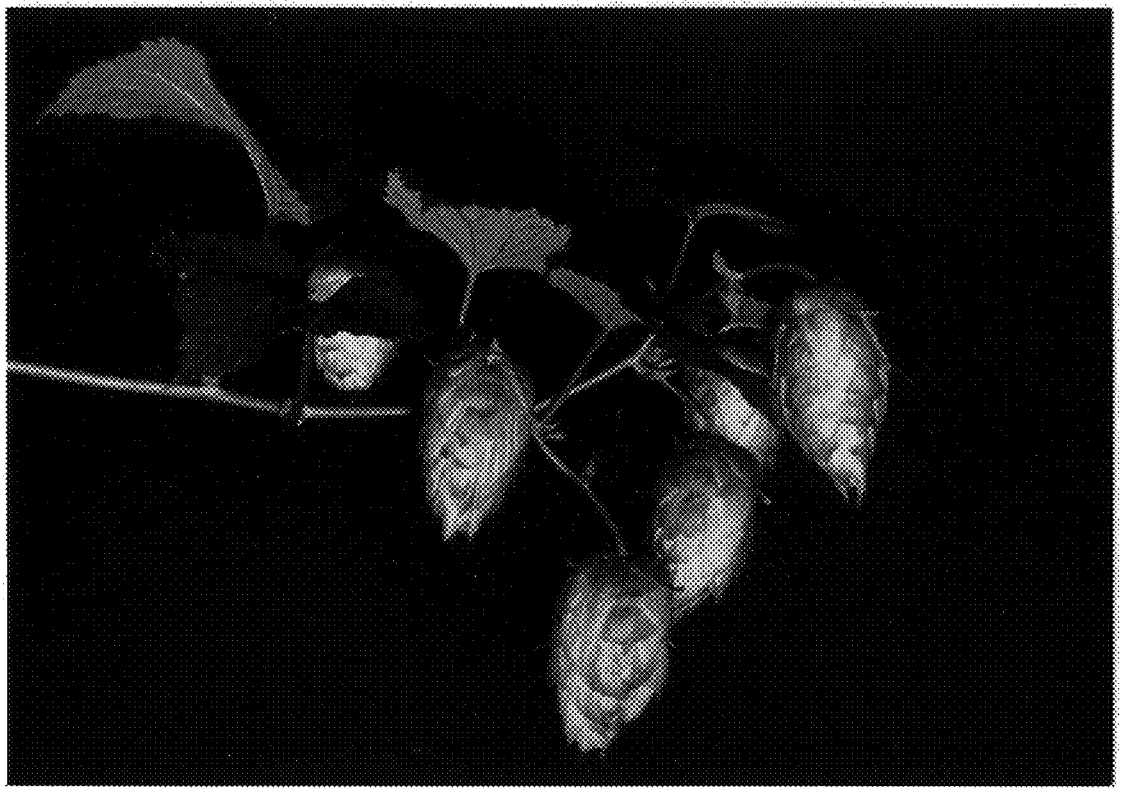
FIG. 2 shows a cluster of hop cones of the new hop variety.
Figure 3:
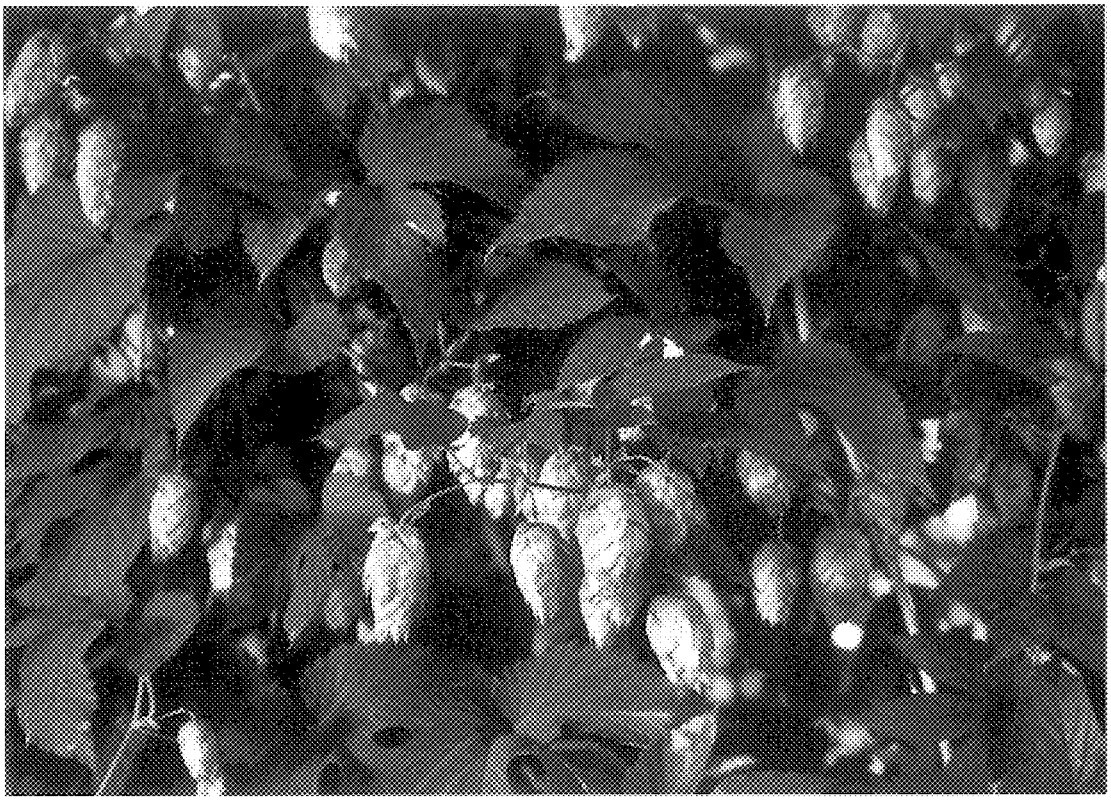
FIG. 3 shows a cluster of hop cones of the new hop variety.
Figure 4:
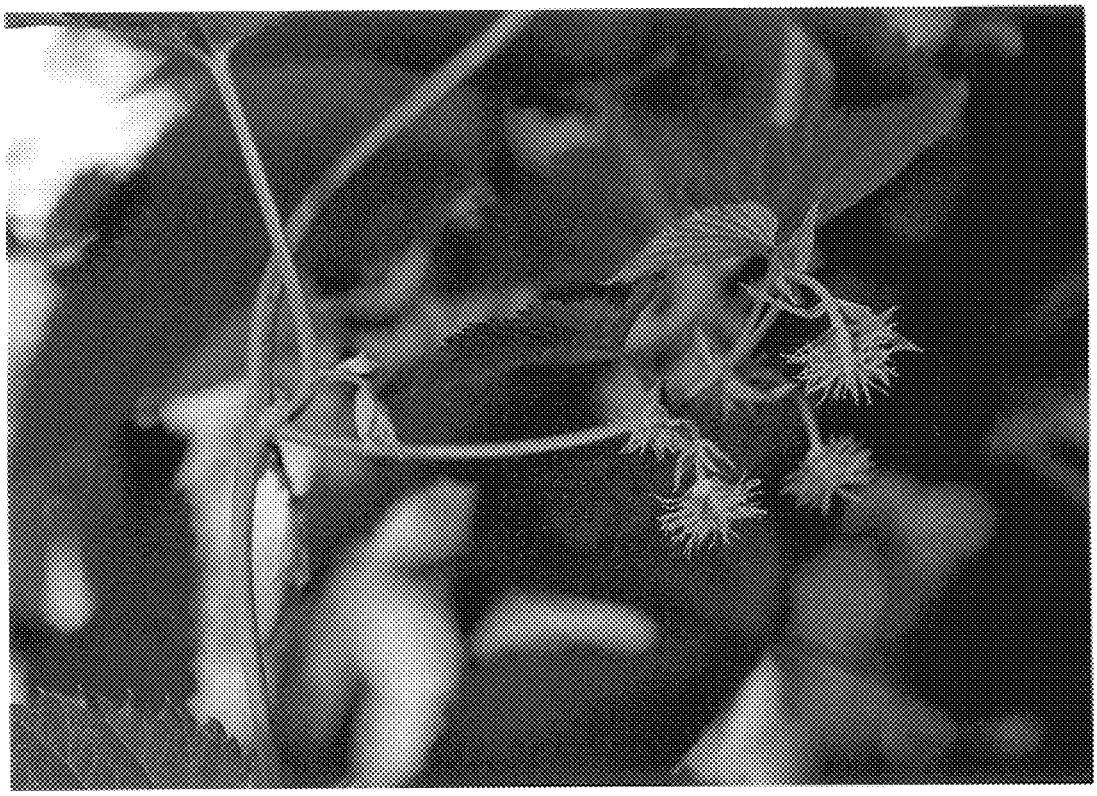
FIG. 4 shows a blossom and leaf of the new hop plant variety.
Figure 5:
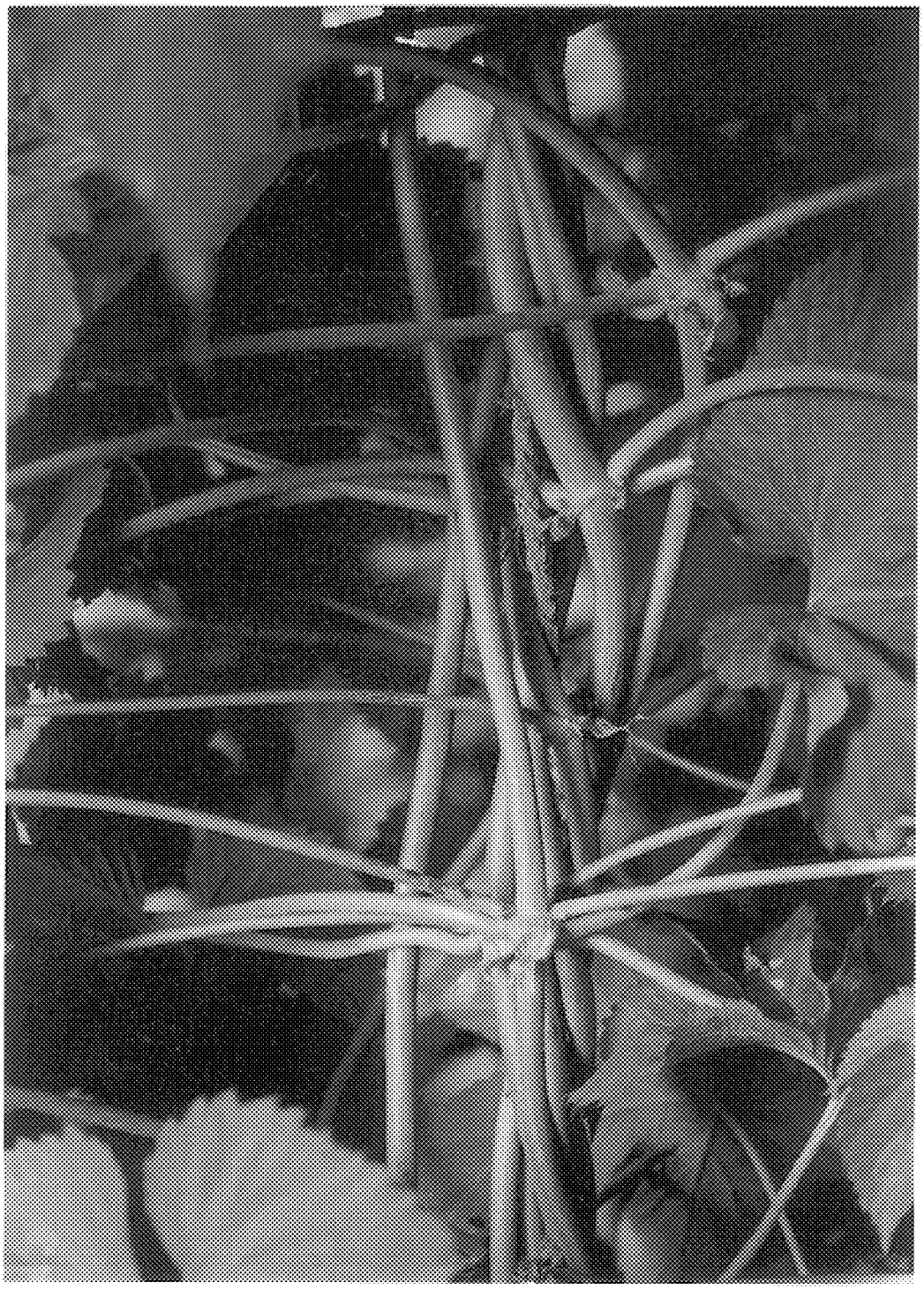
FIG. 5 shows a bine of the new hop plant variety.
Figure 6:
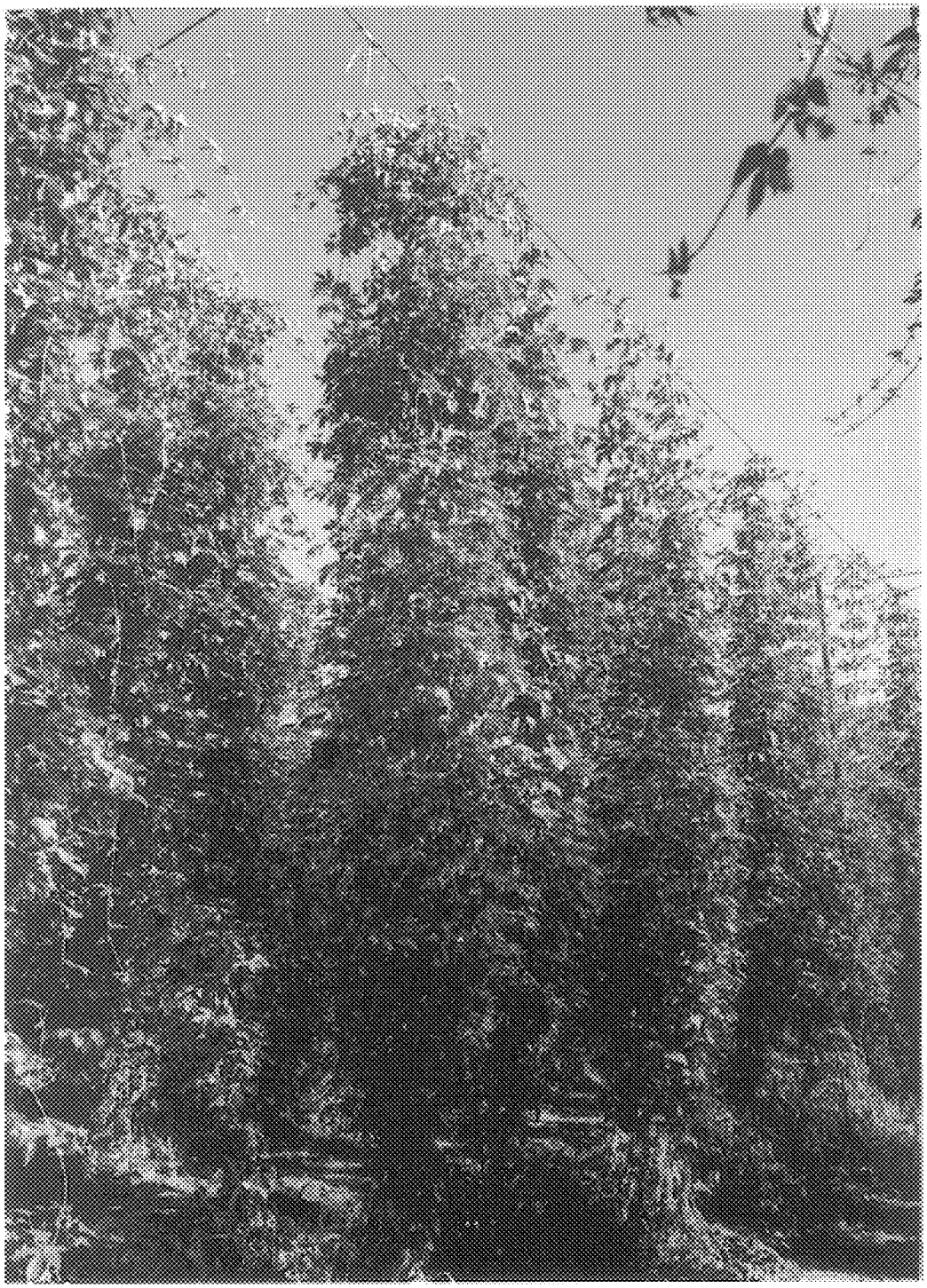
FIG. 6 shows a hop plant of the new variety.

The new hop plant variety is a bittering-type cultivar of recent origin. Its bittering and aromatic properties are similar to the Galena (unpatented) hop variety. However, unlike Galena which is susceptible to powdery mildew, the new variety is moderately tolerant to powdery mildew. It is also tolerant to Sphaerotheca. The new variety produces a medium size cone with fair to good pickability (similar to Galena), and fair to good storageability (25% to 30% alpha loss after six months common storage). Harvest is medium-late (approximately September 5 in Granger Wash.), with a crop yield of 2450 to 2550 pounds per acre (2750 to 2860 kg/ha).

The following is a detailed botanical description of the new and distinct variety of *Humulus lupulus*, based on observations of specimens grown in Grange, Wash. during the 1998 growing season. All colors are described according to The Royal Horticultural Society Colour Chart. It should be understood that the botanical and analytical chemical characteristics described will vary somewhat depending upon cultural practices and climatic conditions and can vary with location and season.

1. Bine:
   - *Color.*—Yellow green (146D).
   - *Stripe.*—None.
   - *Stipule color.*—Yellow green (146D).
   - *Stipule direction.*—Down, forked.
   - *Diameter.*—1.05 cm (measurement taken at 2.75 m).
   - *Shoot emergence.*—Medium early to medium; similar to Galena.
2. Leaves:
   - *Leaf arrangement.*—Opposite.
   - *Leaf shape.*—Cordate to palmate.
   - *Average length.*—18.8 cm.
   - *Average width.*—19.7 cm.
   - *Color — upper surface, mature.*—Green (139A).
   - *Color — lower surface, mature.*—Green (137B).
   - *Color — upper surface, immature.*—Green (139A).
   - *Color — lower surface, immature.*—Green (137B).
   - *Number of leaf lobes.*—1–5.
   - *Margin.*—Serrate.
   - *Serrations per inch.*—5 min., 8 max.
   - *Pose.*—Downward.
   - *Average petiole length.*—8.9 cm.
   - *Venation.*—Palmate.
   - *Vein color.*—Yellow green (146D).
3. Cones:
   - *Average length.*—3.3 cm.
   - *Average diameter.*—1.7 cm.
   - *Color.*—Bract tip: Yellow green (144A). Bract base: Yellow green (145D). Bracteole: Yellow green (145C).
   - *Shape.*—Ovoid.
   - *Bract shape.*—Obovate.
   - *Bract tip shape.*—Mucronate.
   - *Bract tip position.*—Recurved.

*Bracteole shape.*—Oblanceolate.

*Bracteole tip shape.*—Narrowly rounded tip.

*Shattering potential at harvest.*—Similar to Galena.

*% Alpha acids.*—12.0%–14.0% of cone weight (ASBC Spectrophotometric method).

*% Beta acids.*—8.0%–9.0% of cone weight (ASBC Spectrophotometric method).

*% Cohumulone.*—32%–35% of alpha acids.

*Total oils.*—1.5–1.8 mL/100 g.

*Aroma.*—Mild, floral with spicy notes.

4. Technical data: Essential Oil Profile of YCR Accession No. 7: 103 mg of 10% Adsorbate/150C/5 Min. by DTD-GC-MS.

| MS Spec# | Area Integration | Peak Assignment | Area % |
|---|---|---|---|
| 76–212 | 18520 | acetone + isoprene | 0.297 |
| 235–256 | 8148 | 2-methyl-3-buten-1-ol | 0.131 |
| 274 | 412 | pentanal ? | 0.007 |
| 280 | 1051 | hexene | 0.017 |
| 287 | 412 | ? | 0.007 |
| 297 | 189 | ? | 0.003 |
| 302 | 145 | ? | 0.002 |
| 317 | 128 | ? | 0.002 |
| 350 | 2519 | acetic acid | 0.040 |
| 364 | 105 | methylpentanone | 0.002 |
| 371 | 1887 | ? m/z 56, 70 peaks | 0.030 |
| 387 | 166 | ? | 0.003 |
| 404 | 615 | 3-methyl-2-butenal | 0.010 |
| 415 | 466 | hexanal | 0.007 |
| 426 | 3539 | isobutyric acid | 0.057 |
| 432 | 3119 | n-octane | 0.050 |
| 460 | 284 | ? | 0.005 |
| 473 | 229 | isopropylisobutyrate | 0.004 |
| 482 | 7032 | 3-methylbutyric acid | 0.112 |
| 491 | 4103 | 2-methylbutyric acid | 0.066 |
| 505 | 221 | ? m/z 82/81/67 peaks | 0.004 |
| 508 | 877 | ? m/z 81 peak | 0.014 |
| 521 | 14624 | propanoic acid + propylisobutyrate | 0.234 |
| 528 | 1939 | 2,6-dimethyl-2,4-heptadiene | 0.031 |
| 537 | 2721 | 5,5-dimethyl-2(5H)-furanone | 0.044 |
| 546 | 1776 | alpha-pinene | 0.028 |
| 554 | 587 | isobutylisobutyrate | 0.009 |
| 557 | 704 | 4-methylpentanoic acid | 0.011 |
| 562 | 842 | dimethyltrisulfide | 0.013 |
| 569 | 30632 | 2-methylbutylpropanoate | 0.491 |
| 578 | 600 | 6-methyl-5-heptene-2-one | 0.010 |
| 582 | 43591 | beta-pinene + methyl-5-methylhexanoate | 0.698 |
| 595 | 1589016 | myrcene | 25.451 |
| 600 | 2746 | isobutyl-2-methylbutyrate | 0.044 |
| 607 | 38160 | 3-methylbutylisobutyrate | 0.611 |
| 611 | 102594 | 2-methylbutylisobutyrate | 1.643 |
| 615 | 18027 | methylheptanoate | 0.289 |
| 621 | 1084 | ? sulfur-compd. possibly S-methylmethanethiosulphonate | 0.017 |
| 629 | 12559 | limonene + beta-phellandrene | 0.201 |
| 634 | 2067 | ? terpene | 0.033 |
| 645 | 86156 | beta-ocimene + pentyl-2-methylpropanoate | 1.380 |
| 654 | 400 | methyl-2,5-dimethylhexanoate | 0.006 |
| 656 | 665 | gamma-terpinene | 0.011 |
| 662 | 450 | isoctanol | 0.007 |
| 672 | 6486 | heptanoic acid | 0.104 |
| 676 | 51375 | methyl-6-methylheptanoate | 0.823 |
| 682 | 1875 | linalool oxide | 0.030 |
| 686 | 650 | terpinolene | 0.010 |
| 691 | 24253 | linalool + nonanal | 0.388 |
| 697 | 16354 | 2-methylbutyl-2-methylbutyrate | 0.262 |
| 700 | 10821 | pentyl-3-methylbutyrate | 0.173 |
| 704 | 661 | ? sulfur-compd. | 0.011 |
| 713 | 51579 | methyloctanoate | 0.826 |
| 718 | 888 | ? sulfur-compd. | 0.014 |
| 725 | 1636 | 2,3-dihydro-3,5-dihydroxy-6-methyl-4(H)-pyran-4-one | 0.026 |

-continued

| MS Spec# | Area Integration | Peak Assignment | Area % |
|---|---|---|---|
| 734 | 11124 | octanoic acid (branched isomer) | 0.178 |
| 740 | 12989 | hexylisobutyrate | 0.208 |
| 743 | 450 | cis-3-hexenylisobutyrate | 0.007 |
| 745 | 1999 | 2-decanone (branched isomer) | 0.032 |
| 752 | 458 | heptanethioic acid, S-methyl ester | 0.007 |
| 758 | 439 | methylphenylacetate | 0.007 |
| 771 | 22724 | ? m.w. branched alcohol m/z 59 base peak + octanoic acid | 0.364 |
| 779 | 262 | 4,8-dimethylnona-1,7-diene | 0.004 |
| 783 | 16073 | methylnonanoate (branched isomer) | 0.257 |
| 789 | 11463 | methylnonanoate (branched isomer) | 0.184 |
| 795 | 165 | ? | 0.003 |
| 801 | 1728 | heptylpropanoate | 0.028 |
| 807 | 4605 | methylnonenoate | 0.074 |
| 818 | 541 | ? 164 m.w. w/149 base peak (phenolic ?) | 0.009 |
| 824 | 26497 | methylnonanoate | 0.424 |
| 831 | 83 | nerol | 0.001 |
| 841 | 1433 | nonanoic acid (branched isomer) | 0.023 |
| 848 | 347 | ? | 0.006 |
| 853 | 4011 | 2-methylheptylpropanoate | 0.064 |
| 858 | 4500 | geraniol | 0.072 |
| 861 | 12462 | 2-undecanone (branched isomer) | 0.200 |
| 870 | 211 | methyl, 2-methylnonenoate | 0.003 |
| 873 | 222 | 2-undecanol | 0.004 |
| 882 | 11051 | undecenyl alcohol + nonanoic acid | 0.177 |
| 895 | 474 | octenyl acetate | 0.008 |
| 902 | 49630 | methyldecanoate (branched isomer) | 0.795 |
| 905 | 29807 | 2-undecanone | 0.477 |
| 910 | 511 | ? 180 m.w., 95 base peak, possibly bornylformate | 0.008 |
| 921 | 2556 | octylpropanoate | 0.041 |
| 926 | 267900 | methyl-4-decenoate + methyl-4,8-decadienoate | 4.291 |
| 937 | 4377 | methyldecenoate isomer + tridecane | 0.070 |
| 940 | 4657 | methylgeranate | 0.075 |
| 947 | 91720 | methyldecanoate | 1.469 |
| 959 | 2258 | decanoic acid (branched isomer) | 0.036 |
| 976 | 7728 | octyl-2-methylpropanoate | 0.124 |
| 981 | 578 | ? unsaturated alcohol or aldehyde | 0.009 |
| 987 | 6658 | 2-dodecanone (branched isomer) | 0.107 |
| 993 | 15287 | methyl-2-undecenoate | 0.245 |
| 999 | 3411 | alpha-cubebene | 0.055 |
| 1007 | 8331 | decanoic acid | 0.133 |
| 1014 | 15024 | geranyl acetate | 0.241 |
| 1020 | 307 | ? acetate | 0.005 |
| 1024 | 769 | possibly bornylacetate | 0.012 |
| 1029 | 40607 | methylundecanoate (branched isomer) | 0.650 |
| 1034 | 15141 | alpha-ylangene + 2-dodecanone | 0.243 |
| 1038 | 2758 | 2-methydecanoic acid | 0.044 |
| 1048 | 2282 | alpha-copaene | 0.037 |
| 1055 | 2036 | methylundecadienoate | 0.033 |
| 1064 | 3883 | methyl-10-undecenoate | 0.062 |
| 1071 | 665 | ? sesquiterpene 206 m.w. 163 base peak | 0.011 |
| 1076 | 3061 | methylundecanoate | 0.049 |
| 1091 | 755736 | caryophyllene | 12.104 |
| 1100 | 18236 | beta-cubebene | 0.292 |
| 1106 | 718 | linalylisobutyrate | 0.011 |
| 1111 | 1009 | 3-methylbutyloctanoate | 0.016 |
| 1120 | 4584 | 2-tridecanone (branched isomer) | 0.073 |
| 1135 | 1466661 | humulene | 23.491 |
| 1140 | 2713 | ? 204 m.w. sesquiterpene 161 base peak | 0.043 |
| 1145 | 1812 | methyldodecenoate | 0.029 |
| 1156 | 48981 | gamma-muurolene + methyldodecanoate | 0.785 |
| 1165 | 4436 | 2-tridecanone | 0.071 |
| 1170 | 739846 | beta-selinene | 11.850 |
| 1177 | 19970 | methyl-3,6-decadienoate | 0.320 |
| 1183 | 64588 | alpha-selinene | 1.034 |
| 1186 | 28882 | geranyl isobutyrate | 0.463 |
| 1192 | 4917 | methyldodecenoate + delta-cadinene | 0.079 |
| 1202 | 32080 | alpha-muurolene | 0.514 |
| 1206 | 2266 | calamenene | 0.036 |
| 1213 | 54844 | beta-cadinene | 0.878 |
| 1225 | 4495 | delta-selinene | 0.072 |

-continued

| MS Spec# | Area Integration | Peak Assignment | Area % |
|---|---|---|---|
| 1232 | 10491 | sesquiterpene w/no common name CAS#16728-99-7, cadinene-type | 0.168 |
| 1242 | 4032 | selina-3,7-diene (eudesma-3,7-diene) | 0.065 |
| 1250 | 201 | 2-tetradecanone (branched isomer) | 0.003 |
| 1258 | 6066 | elixene | 0.097 |
| 1264 | 284 | ? | 0.005 |
| 1268 | 139 | caryophyllyl alcohol | 0.002 |
| 1282 | 10530 | caryophyllene oxide | 0.169 |
| 1293 | 300 | methyltridecadienoate | 0.005 |
| 1299 | 1823 | humulene epoxide | 0.029 |
| 1304 | 307 | methyridecenoate | 0.005 |
| 1313 | 18259 | humulene epoxide | 0.292 |
| 1319 | 1141 | globulol | 0.018 |
| 1324 | 1521 | ? 222 m.w. sesquiterpene | 0.024 |
| 1339 | 6389 | delta-cadinol | 0.102 |

-continued

| MS Spec# | Area Integration | Peak Assignment | Area % |
|---|---|---|---|
| 1351 | 8125 | cadinol | 0.130 |
| 1363 | 1200 | eudesmol | 0.019 |
| 1366 | 12410 | Juniper Camphor (eudesma-7-en-4-ol) | 0.199 |
| 1387 | 378 | geranyl ester ? | 0.006 |
| 1391 | 145 | ? | 0.002 |
| 1439 | 198 | ? | 0.003 |
| 1520 | 1897 | ? 250 m.w. w/115 base peak | 0.030 |
| | 6243539 | Total Essential Oil Components | 100.000 |

I claim:

1. A new variety of hop plant substantially as herein shown and described.

* * * * *

UNITED STATES PATENT AND TRADEMARK OFFICE

CERTIFICATE OF CORRECTION

PATENT NO. : PP 12,401 P2
DATED : February 12, 2002
INVENTOR(S) : Charles E. Zimmermann It is certified that error appears in the above-identified patent and that said Letters Patent is hereby corrected as shown below:

Title page,
Item [73], Assignee, replace "Sunnyvale, CA" with -- Sunnyside, WA --.

Signed and Sealed this

Seventeenth Day of September, 2002

*Attest:*

*Attesting Officer*

JAMES E. ROGAN
*Director of the United States Patent and Trademark Office*